Figure 1A:
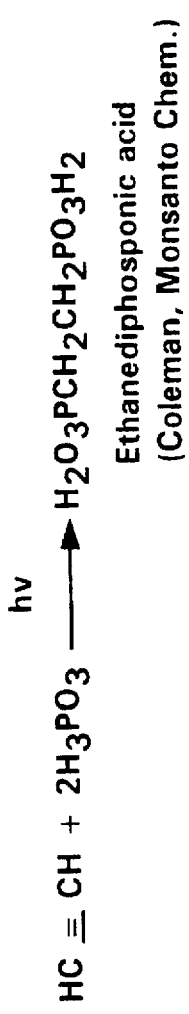

United States Patent [19]
Kneller et al.

[11] Patent Number: 5,783,728
[45] Date of Patent: Jul. 21, 1998

[54] PHOSPHINATE COMPOUNDS PREPARED FROM ACETYLENIC COMPOUNDS AND INORGANIC PHOSPHITE SALTS AND DERIVATIVES OF THESE COMPOUNDS

[75] Inventors: James F. Kneller, LaGrange Park; Donald A. Johnson, Batavia; Vytas Narutis, Riverside; Binaifer S. Khambatta, Orland Park, all of Ill.

[73] Assignee: Nalco Chemical Company, Naperville, Ill.

[21] Appl. No.: 779,581

[22] Filed: Jan. 7, 1997

Related U.S. Application Data

[62] Division of Ser. No. 235,734, Apr. 29, 1994, Pat. No. 5,647,995.

[51] Int. Cl.$^6$ ............................................. C07F 9/22
[52] U.S. Cl. .............................. 562/21; 562/20; 560/179
[58] Field of Search ................... 562/20, 21; 560/179

[56] References Cited

U.S. PATENT DOCUMENTS

| | | | |
|---|---|---|---|
| 3,617,576 | 11/1971 | Kerst | 210/58 |
| 4,159,946 | 7/1979 | Smith et al. | 210/58 |
| 4,246,103 | 1/1981 | Block et al. | 210/699 |
| 4,497,713 | 2/1985 | Geiger et al. | 210/699 |
| 4,590,014 | 5/1986 | Wolf et al. | 260/502.4 R |
| 5,167,828 | 12/1992 | Emmons et al. | 210/700 |
| 5,386,038 | 1/1995 | Davis et al. | 549/262 |

OTHER PUBLICATIONS

CA 100:51700 (1983).

Primary Examiner—Paul J. Killos
Attorney, Agent, or Firm—Thomas M. Breininger; Elaine M. Ramesh

[57] ABSTRACT

An improved method is disclosed for the preparation of novel alkali metal diphosphinate salts by the reaction of an acetylenic compound with an alkali metal hypophosphite in the presence of a free radical source, the use of these novel compounds in further reactions to prepare diphosphonate compounds and diphosphinate containing adducts, oligomers and polymers and utilization of these compounds, polymers and oligomers to control calcium carbonate scale and mild steel corrosion in cooling water.

24 Claims, 7 Drawing Sheets

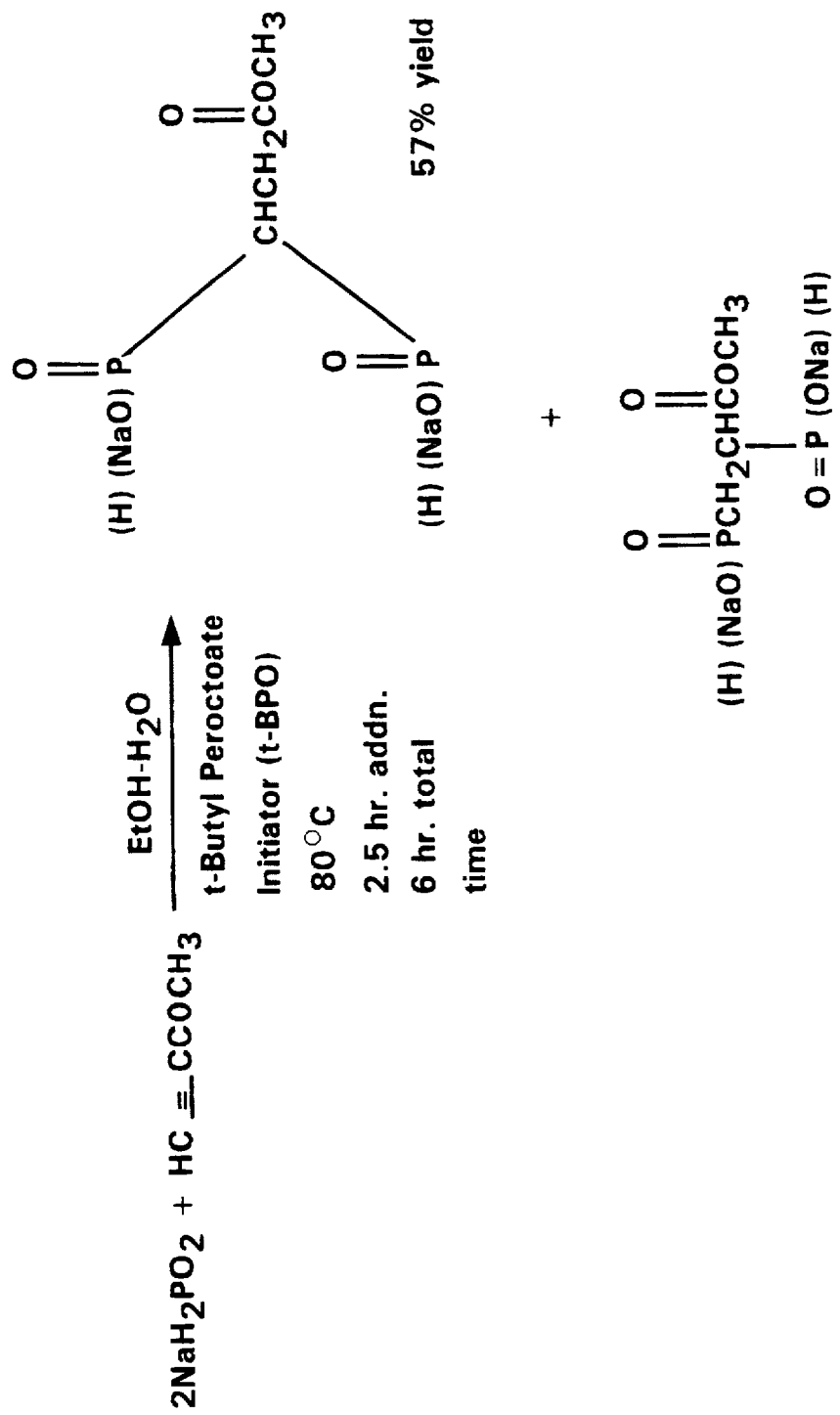

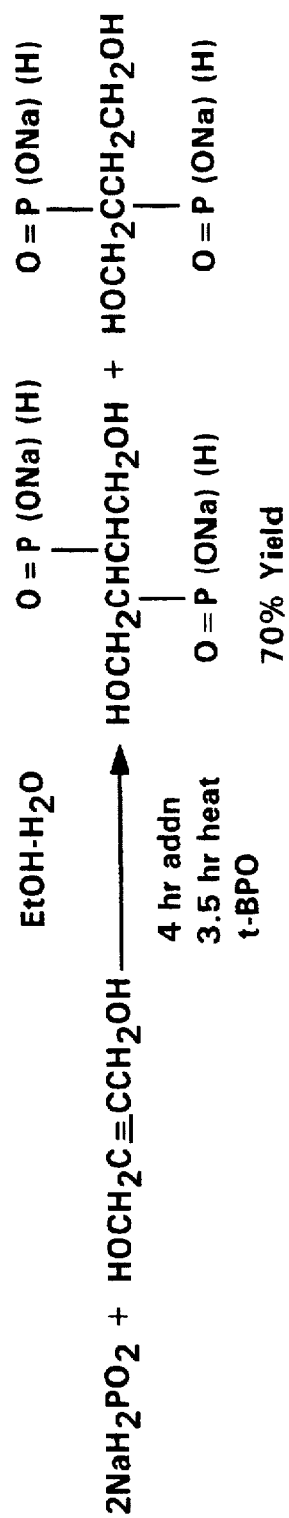

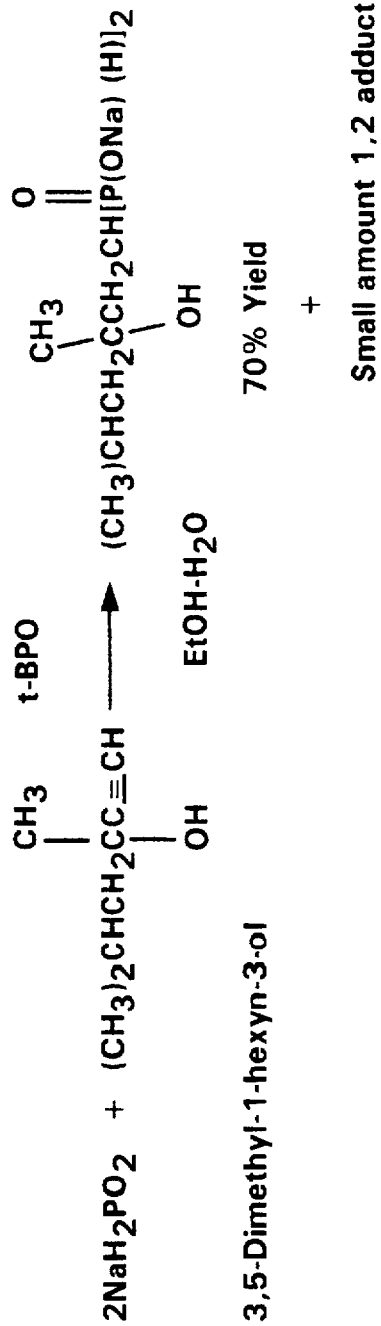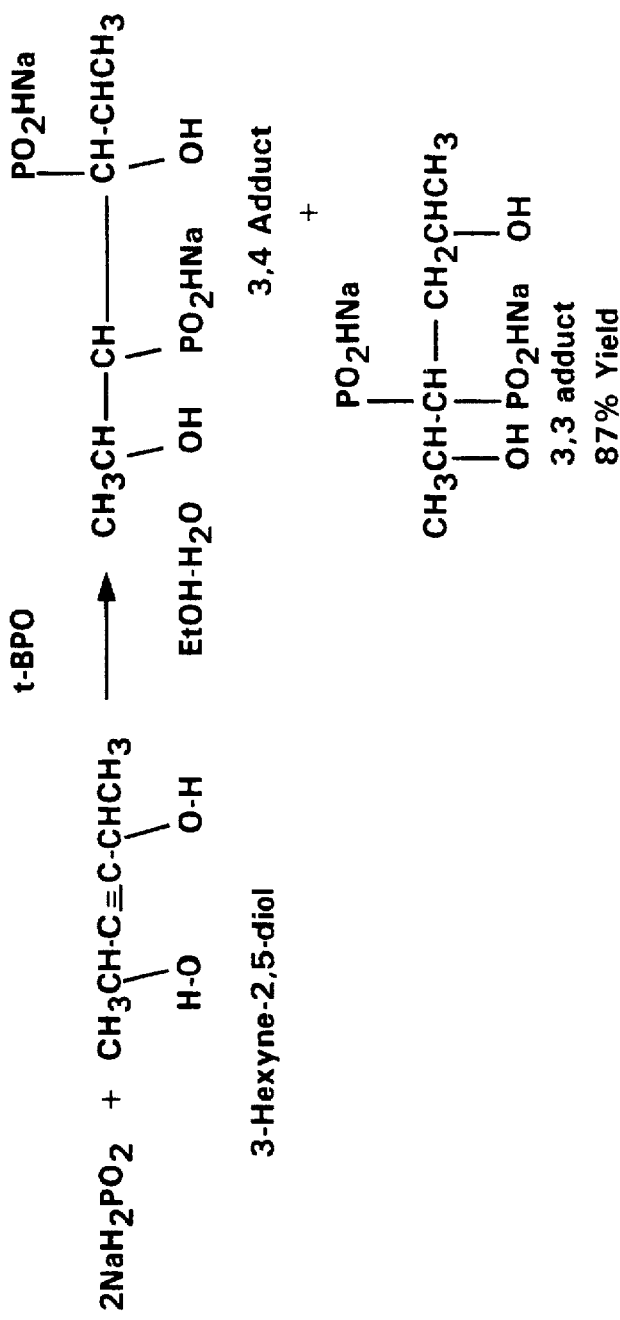

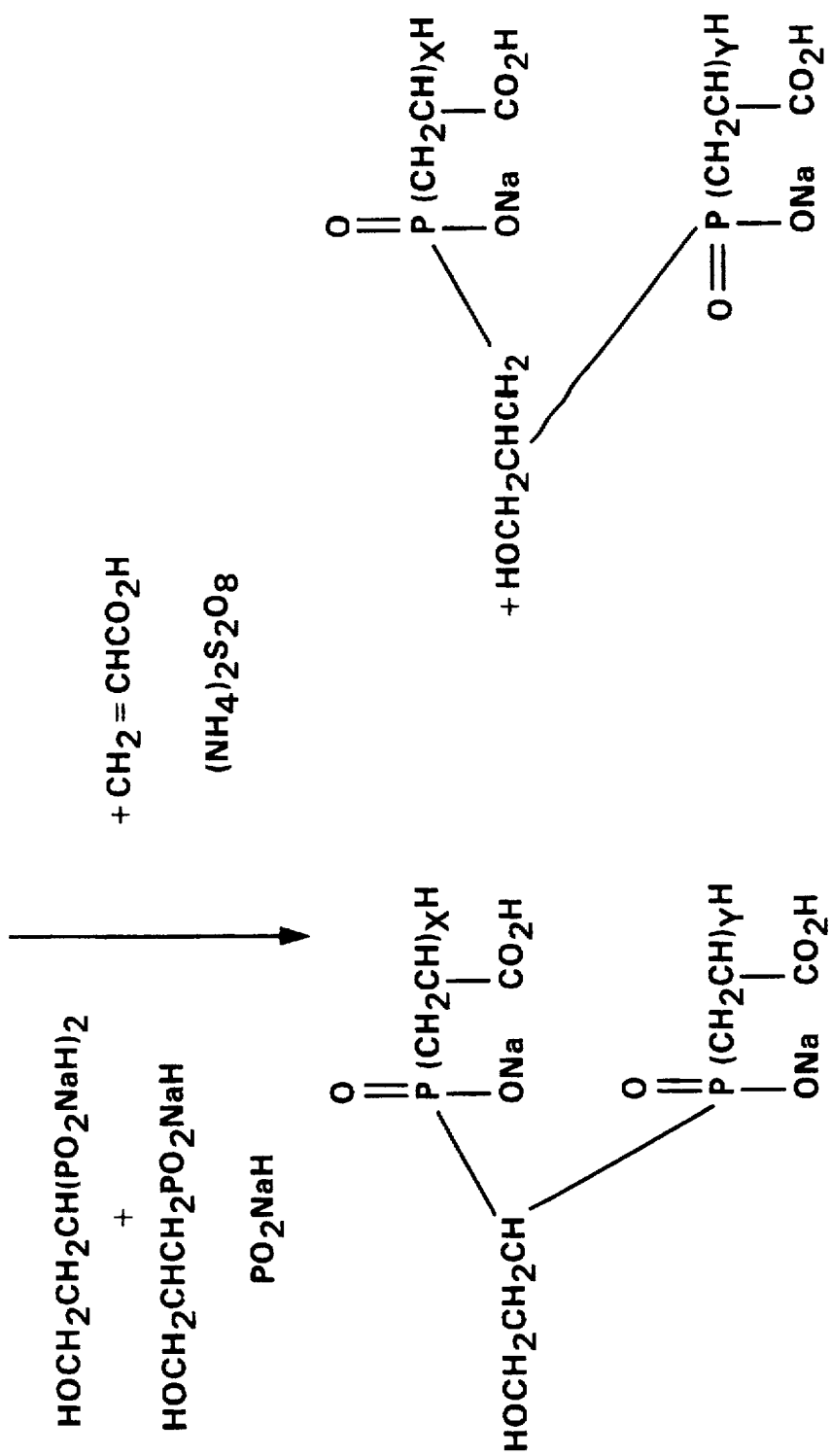

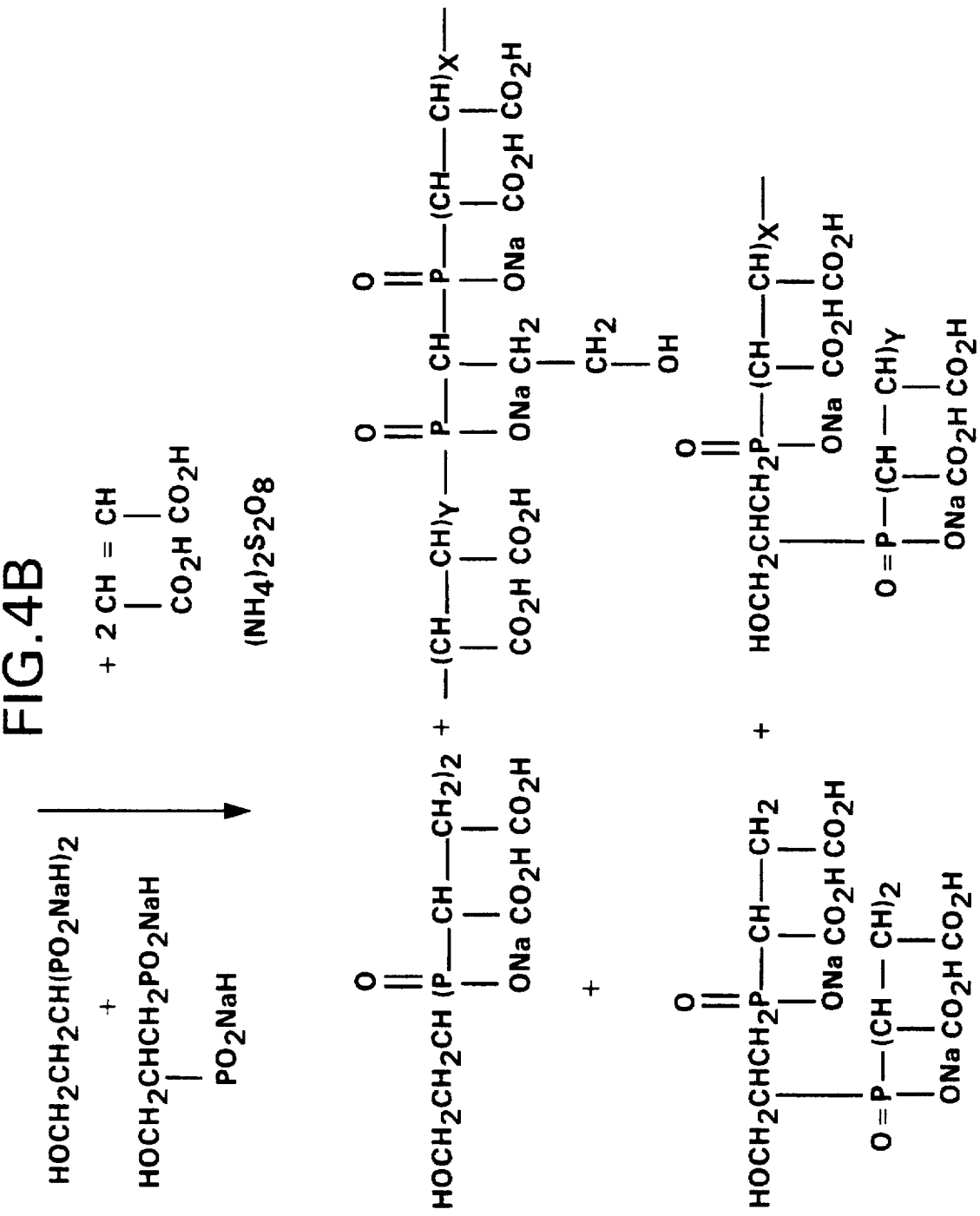

PHOSPHINATE COMPOUNDS PREPARED FROM ACETYLENIC COMPOUNDS AND INORGANIC PHOSPHITE SALTS AND DERIVATIVES OF THESE COMPOUNDS

This application is a division of application number 08/235734, filed Apr. 29, 1994, now U.S. Pat. No. 5,647,995.

BACKGROUND OF THE INVENTION

The present invention relates to a novel method for producing unique phosphite salts.

INTRODUCTION

Additions of hypophosphorus acid and sodium hypophosphite to olefinic compounds are well known but yields have not been good and side reactions (telomerization, double addition, oxidation of hypophosphorus acid) occur. The reactions were frequently run under pressure and required long reaction times. Recently an improved method for addition of sodium hypophosphite to olefin was reported in U.S. Pat. No. 4,590,014. This involved slow addition of the olefin and a free radical source in alcohol solution to an aqueous-alcohol solution of sodium hypophosphite. Yields of 80% to 100% were reported for 1-olefins, cyclohexene and dimethyl maleate. The reactions required no pressure apparatus and were completed in five to eight hours in most cases.

THE DRAWINGS

Figure 1B:
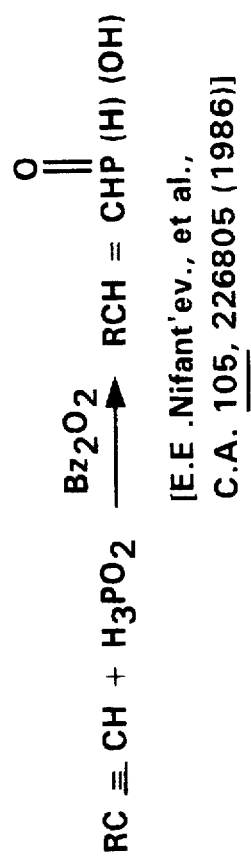
Figure 1C:
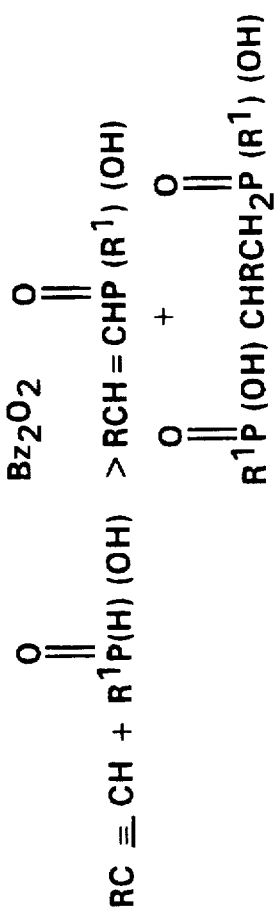
Figure 2C:
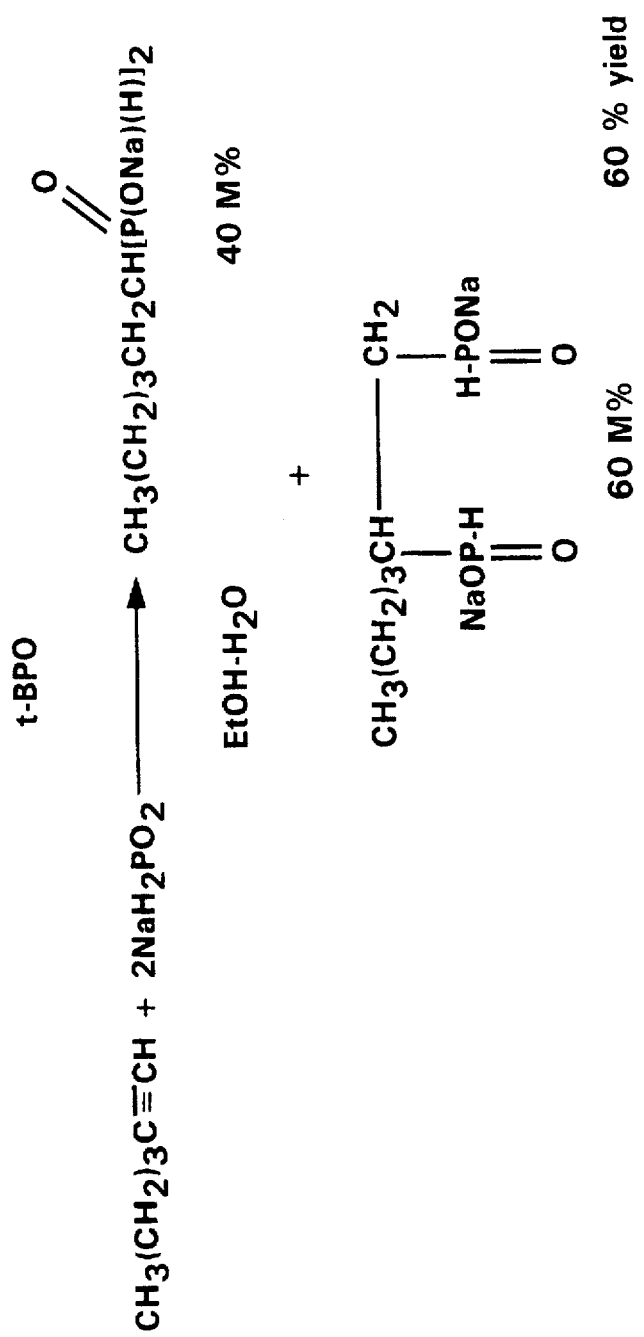

FIGS. 1–3 show the preparation of several novel phosphinates using the synthesis methods of the invention. Also shown are prior art reactions of acetylenic compounds with inorganic acids of phosphorus. FIG. 4 shows the preparation of novel polycarboxylic diphosphinate products.

PRIOR ART

Ethanediphosphonic acid (Reaction 1, FIG. 1) was prepared directly from acetylene and phosphorous acid using U.V. light catalysis (Coleman, Monsanto). Nifant'ev, et al reacted acetylenic compounds with hypophosphorous acid and found that monoaddition of hypophosphorous acid was the main reaction (Reaction 2, FIG. 1) even when 6 fold excess of hypophosphorous acid was used. However, phosphinic acids added to acetylenes give both mono and diadducts (Reaction 3, FIG. 1). In the present invention, sodium hypophosphite was used and readily added to acetylenes to form diadducts in good yields.

THE INVENTION

The invention comprises in its broadest aspect:
a method for making compounds having the formula:

$$[(NaO)(H)(O)P]_x \quad [P(O)(H)(ONa)]_y$$
$$| \quad\quad\quad\quad |$$
$$RC(H)_w — C(H)_z R'$$

and mixtures thereof where R and R' are radicals from the group consisting of H, alkyl, hydroxyalkyl, alkyl carboxylate, carboxyl, carboxylate, cycloaliphatic and substituted cycloaliphatic, phenyl and substituted phenyl, and each do not contain more than 18 carbon atoms, x and y are integers ranging from 0–2 with the sum of x+y being equal to 2, w and z are integers having a value ranging from 0–2 which comprises the steps of reacting a compound of the formula:

with at least two moles of sodium hypophosphite in the presence of polar solvent soluble free radical catalyst and then recovering the produced compounds.

These organodiphosphinic compounds as initially synthesized are in the form of mixtures of two easily recoverable compounds. These mixtures are represented by the formulas:

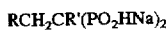

and

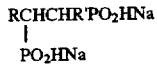

with R and R' having the same values previously described.

The phosphinate compounds covered by the above formula are believed to represent new compounds. This is particularly true with respect to compounds where one occurrence R and R'0 are hydroxyalkyl groups which contain from between 3–12 carbon atoms. Typical of compounds readily prepared by the process described herein and covered by the above structural formula would be those compounds where R' is either R or H and R is a radical such as:

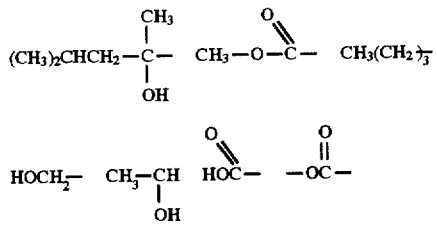

It is understood that the values for R & R' described above apply to the starting acetylenic compounds and the organic phosphinates produced by the method of the invention.

THE PREFERRED STARTING HYDROXYALKYL SUBSTITUTED ACETYLENIC COMPOUNDS

For a list of acetylenic alcohols that may be used in the process of the invention to prepare several unique phosphinates reference may be had to Table 1.

TABLE 1

Acetylenic Alcohols

Compound No.

1. (2,4,7,9-tetramethyl-5-decyn-4,7-diol)

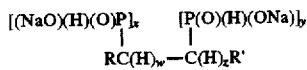

2. Methyl Butynol
   (3-Methyl-1-butyn-3-ol)

$(CH_3)_2CC \equiv CH$
   $\quad |$
   $\quad OH$

TABLE 1-continued

Acetylenic Alcohols

Compound No.

3. Methyl Pentynol
   (3-methyl-1-pentyn-3-ol)

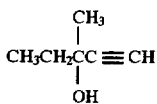

4. Ethyl Octynol
   (4-ethyl-1-octyn-3-ol)

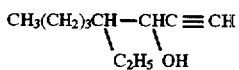

5. (3,6-dimethyl-4-octyne-3,6-diol)

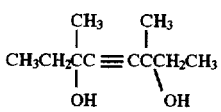

6. (3,5-dimethyl-1-hexyn-3-ol)

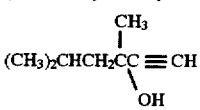

7. Composition No. 1 + 40 wt. % E.O.)
   (Or 3.5 moles E.O.)

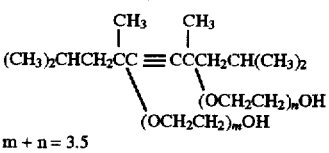

m + n = 3.5

8. Dimethyl Hexynediol
   (2,5-dimethyl-3-hexyn-2,5-diol)

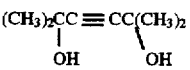

9. Hexynol
   (1-hexyn-3-ol)

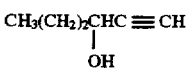

10. Ethynynl Cyclohexanol
    (1-ethynyl-1-cyclohexanol)

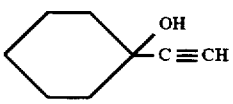

THE HYPOPHOSPHITE SALT

Sodium hypophosphite, which is employed in the present method as its stable monohydrate, is the preferred hypophosphite salt for use in the present invention. When sodium hypophosphite is used as the hypophosphite salt, a sodium phosphinate will be isolated as the reaction product. Although it will generally be preferred that the present method be directed toward the preparation of sodium phosphinates due to their high water solubility, stability and low cost, for some applications the preparation of other alkali metal or alkaline earth metal phosphinates may be desirable. In such cases, other alkali metal hypophosphites such as lithium hypophosphite, potassium hypophosphite, rubidium hypophosphite, or cesium hypophosphite may be employed in the present reaction with the appropriate adjustment in the solvent system, reaction temperature and the like.

In the present method the molar ratio of acetylenic material to hypophosphite salt will be at least 1:2. Most preferably the molar ratio of acetylenic material to hypophosphite salt will use slightly more than 2 moles of the hypophosphite.

THE FREE RADICAL INITIATOR

In the present invention a solution of the hypophosphite salt is treated with the acetylenic component in the presence of an amount of a free radical source effective to catalyze the reaction between the hypophosphite anion and the acetylenic triple bond. Any of the common free radical sources including organic peroxides such as benzoyl peroxide or diazo compounds such as 2.2'azobisisobutyronitrile (AIBN) may be employed in the practice of the present invention. Organic peroxyesters are the preferred initiators. Useful commercially available peroxyesters include the alkylesters of peroxycarboxylic acids, the alkylesters of monoperoxydicarboxylic acids, the dialkylesters of diperoxydicarboxylic acids, the alkylesters of monoperoxycarbonic acids, and the alkylene diesters of peroxycarboxylic acids. Among these classes of peroxyesters the alkylesters of peroxycarboxylic acids and the alkylesters of monoperoxydicarboxylic acids are preferred in the practice of the present invention. The former class of peroxyesters includes t-butyl peroctoate, t-butyl perbenzoate and t-butyl peroxyneodecanoate, while the latter class includes compounds such as t-butyl peroxymaleic acid. These compounds are commercially available from Pennwalt Chemicals, Buffalo, N.Y. The amount of any free radical initiator required to catalyze the acetylenic-hypophosphite reaction will vary depending upon the molecular weight of the initiator and its thermal stability. In the case of the peroxyesters, mole ratios of acetylenic to peroxyester of 10 to 1 or more have been found to provide acceptable reaction rates.

THE SOLVENT SYSTEM

In the practice of the present invention the solvent system can be chosen with the decomposition temperature of the reaction promoter in mind. A solution of hypophosphite is typically maintained at a constant temperature while the acetylenic component and the free radical initiator are simultaneously added into the reaction vessel containing the hypophosphite solution. Preferably the hypophosphite solution will be maintained at a temperature at or slightly above the decomposition point of the free radical initiator compound. This temperature will be selected on the basis of the known decomposition temperature of the free radical initiator compound and will preferably be established by means of a refluxing azeotropic organic solvent system. The most commonly employed azeotropic solvent systems for use in the present invention are mixtures of alkanols and water. For example, mixtures of ethanol and water within the range of about 2–8 parts ethanol to each part of water can be compounded so as to reflux at temperatures of about 70–80 degrees C. A mixture of about 300 grams of reagent alcohol (a mixture of 95% denatured ethanol with 5% isopropyl alcohol) and 100 ml of water will reflux at a temperature of about 78 degrees C. Other organic alcohol-water systems may be selected which will reflux at temperatures at or slightly above the decomposition points of organic peroxyesters useful to initiate the present reaction, e.g. within the range of about 50–100 degrees C. Other alcohols useful as the organic component of the present solvent systems include methanol, isopropanol, t-butanol and the like.

GENERAL REACTION CONDITIONS

In the practice of the present invention the hypophosphite salt is first dissolved in the organic solvent system and the solution brought to a temperature at or slightly above the decomposition point of the free radical initiator compound. The acetylenic material and the free radical initiator are then slowly and simultaneously added to the heated, stirred hypophosphite solution. Preferably the acetylenic component and the free radical initiator compound are dissolved in an organic solvent which is the same as or is compatible with that used to dissolve the hypophosphite salt. Most preferably the acetylenic compound and the free radical initiator will be added to the hypophosphite solution in a dropwise fashion or could be added using a pump after having been codissolved in the same solvent. However, separate solvent streams of the acetylenic compound and the initiator may be introduced into the hypophosphite solution so long as the introduction is substantially simultaneous. Once the organic compound and the free radical initiator have been introduced into the heated hypophosphite solution the temperature of the reaction mixture, the combined solutions, is maintained at or about the pre-selected temperature for a period of time effective to complete the reaction. For example, when a peroxyester is employed to initiate the reaction of a terminal acetylenic or internal acetylenic compound with sodium hypophosphite the typical reaction time will be within the range of about 1.5 to 10 hours preferably about 2 to 8 hours. At the end of this reaction time the phosphinate salt is isolated simply by evaporating the solvents and drying the resulting solid salt in vacuo. In some cases, usually with terminal acetylenic compounds, the main product precipitated and was filtered off. The extent of reaction between the hypophosphite and the acetylenic material to form the phosphinate is easily determinable by $^{31}$p NMR. The use of the preferred reaction times in the present method typically provides yields of phosphinate salts on the order of 55 to 100%. These yields are attained at reaction times which are one or two orders of magnitude less than those taught to be optimal by the prior art.

The present invention will be further illustrated by reference to the following detailed examples.

EXAMPLE 1

In light of the known addition of hypophosphorus acid to acetylenes and the improvement in yield and ease of reaction of sodium hypophosphite additions to olefins, it seemed possible that two moles of sodium hypophosphite could be added to acetylenes. This reaction was expected to go better with a terminal rather than an internal acetylene so the first reaction was attempted with methyl propiolate and two moles of sodium hypophosphite in alcohol-H$_2$O solvent as shown below.

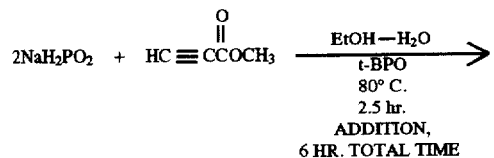

-continued

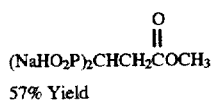

57% Yield

Tertiary butyl peroctoate (TBPO) initiator was used and the initiator and acetylenic compound were dissolved together in denatured ethanol and added over 2.5 hours to a denatured ethanol-water solution (2:1 wt. ratio) of sodium hypophosphite monohydrate. Heating at 80° C. was maintained throughout the addition and for 3.5 hours afterward. During the addition and post heat, a precipitate was formed. At the end of the reaction the white solid precipitate was filtered off and dried in a vacuum. This precipitate was identified by $^{31}$p NMR as nearly pure disodium methyl 3,3-diphosphinicopropionate, the product resulting from 1,1 diaddition of hypophosphite to the methyl propiolate triple bond.

EXAMPLE 2

Synthesis of Diphosphinic Compounds from Acetylenes

Additional diphosphinic compounds were prepared from a variety of common acetylenes as shown in Table 2 and FIGS. 1–3 The same easy procedure was used that was employed to react methyl propiolate with two moles of sodium hypophosphite (Example 1) and as was described in the General Reaction Conditions section. In all cases t-butyl peroctoate (t-BPO) initiator and the acetylene were dissolved together in ethanol and were added slowly to a water-ethanol solution (usually 1:2 weight ratio respectively) of sodium hypophosphite. All reactions were run at the reflux temperature of the ethanol-water azeotrope (80° C.). After the addition was completed (2.5 –3.5 hours), heating at reflux was continued (4–10 hours).

In many of the hypophosphite-acetylene addition reactions, a precipitate of adduct formed as the reaction progressed. The precipitated material resulting from hypophosphite addition to methyl propiolate (Example 1) was found to be only 1,1 adduct based on C-13 and P-31 NMR analysis. Unreacted sodium hypophosphite and possibly a little 1,2 adduct remained in the filtrate. With the propargyl alcohol—NaH$_2$PO$_2$ reaction (Example 3), a fine precipitate formed which was difficult to filter. Phosphorus 31 NMR analysis of this precipitate indicated that it was a mixture of 1,1 and 1,2 adduct in about equimolar amounts. The filtrate contained a small amount of organophosphorus compounds and was mostly unreacted sodium hypophosphite and other inorganic phosphorus compounds. In the reaction of sodium hypophosphite with 3,5-dimethyl-1-hexyn-3-ol (Example 4) again the 1,1-adduct precipitated leaving a small amount of 1,2 adduct and inorganic phosphorus compounds in the filtrate. With 1-hexyne (Example 6), the adduct that precipitated was again the product of 1,1-addition with 1,2 adduct left in the filtrate, based on P-31 NMR analysis. Reaction of two moles of sodium hypophosphite with 2-butyn-1,4-diol (Example 5) did not result in precipitation of the adduct. Instead a two phase system formed with organophosphorus compounds found in each layer. Both layers contained some 2,2 and some 2,3-diadduct of hypophosphite to the butynediol triple bond. Reaction of another internal acetylenic bond compound, 3-hexyne-2,5-diol (Example 7), with two moles of sodium hypophosphite also did not result in precipitation of the adduct. No acetylenic compound was left when the reaction mixture was concentrated to dryness to obtain the product. The $^{31}$p NMR showed multiple P-H bond containing compounds present too numerous to be identifiable. This result might be expected if both 3,3 and 3,4 adducts were formed. With the 3,3 adduct, two asymmetric carbons are present so that two pairs of diastereomers can exist. The 3,4 adduct contains four asymmetric carbons so that four pairs of diastereomers can be present.

Although only a relatively few acetylenic compounds have been reacted with two moles of sodium hypophosphite, some patterns of reaction behavior were observed. For 1-alkyne compounds, the diphosphinic salt usually precipitates in the reaction medium (normally about 67 WT % ethanol-33 WT % water). The precipitating product is usually pure 1,1-adduct or highly enriched 1,1-adduct, probably because 1,1-adducts are more polar and less soluble in ethanol-water than 1,2-adducts. Both 1,1 and 1,2-diphosphinic adducts form but the 1,1-adduct is favored if the 2 carbon of the 1-alkyne is hindered as with 3,5-dimethyl-1-hexyn-3-ol (Example 4) and methyl propiolate (Example 1). With internal acetylenic compounds [2-butyn-1,4-diol (Example 5) and 3-hexyne-2,5-diol (Example 7)] both 1,1 and 1,2 type addition occurs and the product mixture is soluble in the solvent.

Yields of these reactions were good, ranging from 60–100% based on the acetylenic compound. Increasing addition time of the acetylene-initiator-ethanol solution and increasing post addition holding time increased the yield in some cases. Reaction temperature was controlled by the reflux temperature of the water-ethanol azeotrope as was described in U.S. Pat. No. 4,590,014. No other alcohols were tried but these could be used if a different reaction temperature is desired. Since the alcohol-water reflux temperature determines the temperature of the reaction, a free radical initiator was chosen which decomposed conveniently at about 80° C. Tertiary butyl peroctoate has a half life of about 4 hours at 80° C. and use of t-butyl peroctoate resulted in the best yields for addition of sodium hypophosphite to alpha olefins. Other imitators such as Vazo 64, t-butylperoxymaleic acid, t-butyl perbenzoate and t-butyl peroxyneodecanoate may be used.

TABLE 2

PHOSPHINIC COMPOUNDS DERIVED FROM ACETYLENES $$RC \equiv CR' + 2NaH_2PO_2 \xrightarrow[EtOH + H_2O]{F.R. INIT.} \begin{array}{cc} RCH\text{------}CHR' \\ | \quad\quad | \\ O=P-H \quad H-P=O \\ | \quad\quad | \\ ONa \quad\quad ONa \end{array}$$

$$+$$

$$RCH_2-CR'(\overset{O}{\underset{|}{\overset{\|}{P}}}-H)_2$$
$$ONa$$

| EX. | ACETYLENIC COMPOUND | PHOSPHINIC COMPOUND | COMMENTS, YIELDS, ANALYSIS |
|---|---|---|---|
|  | HOCH$_2$C $\equiv$ CCH$_2$OH<br>2-Butyne-1,4-diol | HOCH$_2$CH=CCH$_2$OH<br>\|<br>P(O)(H)(ONa) | 60° C. React. Temp, aq. Soln.<br>(NH$_4$)$_2$S$_2$O$_8$ init., 15% yield |
| 5 | HOCH$_2$C $\equiv$ CCH$_2$OH<br>2-Butyne-1,4-diol | HOCH$_2$CH$_2$C[P(O)(H)(ONa)]$_2$CH$_2$OH<br>+<br>HOCH$_2$CHCHCH$_2$OH<br>\| \|<br>(NaO)(H)(O)P  P(O)(H)(ONa) | 80° C. React. Temp. ETOH—H$_2$O<br>Soln t-BPO init., 70% yield, P-31<br>NMR shows 2,3 adduct and 2,2<br>adduct |
| 1 | CH$_3$O$_2$CC $\equiv$ CH<br>Methyl propiolate | CH$_3$O$_2$CCH$_2$CH[P(O)(H)(ONa)]$_2$ | 60% yield All 1,1 adduct, P-31 NMR |
|  |  | NaO$_2$CCH$_2$CH[P(O)(H)(ONa)]$_2$ | Hydrolysis of Ex. 1 |
| 3 | HOCH$_2$C $\equiv$ CH<br>Propargyl alcohol | HOCH$_2$CH$_2$CH[P(O)(H)(ONa)]$_2$<br>+<br>HOCH$_2$CHCH$_2$<br>\| \|<br>(NaO(H)(O)P  P(O)(H)(ONa) | Get 50:50 M % mixture of 1,1 and<br>1,2 adducts 90% yield P-31 NMR |
| 4 | CH$_2$<br>\|<br>(CH$_3$)$_2$CHCH$_2$CC $\equiv$ CH<br>\|<br>OH<br>3,5-Dimethyl-1-hexyn-3-ol | CH$_3$<br>\|<br>(CH$_3$)$_2$CHCH$_2$CCH$_2$CH[P(O)(H)(ONa)]$_2$<br>\|<br>OH | 1,1 adduct precips. from ethanol<br>H$_2$O, 70% yield, C-13 NMR, P-31<br>NMR |
| 6 | CH$_3$(CH$_2$)$_3$C $\equiv$ CH<br>1-hexyne | CH$_3$(CH$_2$)$_4$CH[P(O)(H)(ONa)]$_2$<br>+<br>CH$_3$(CH$_2$)$_3$CHCH$_2$<br>\| \|<br>(NaO)(H)(O)P  P(O)(H)(ONa) | 1,1 adduct precips. from EtOH H$_2$O,<br>24–30% yield of 1,1 adduct, 77%<br>overall yield, C-13 and P-31 NMR,<br>40M % 1,1-60M % 1,2 adducts |

TABLE 2-continued

PHOSPHINIC COMPOUNDS DERIVED FROM ACETYLENES $$RC \equiv CR' + 2NaH_2PO_2 \xrightarrow[EtOH + H_2O]{F.R. INIT.} \begin{array}{c} RCH\text{------}CHR' \\ | \quad\quad\quad | \\ O=P-H \quad H-P=O \\ | \quad\quad\quad | \\ ONa \quad\quad ONa \end{array}$$

$$+$$

$$\begin{array}{c} O \\ \| \\ RCH_2-CR'(P-H)_2 \\ | \\ ONa \end{array}$$

| EX. | ACETYLENIC COMPOUND | PHOSPHINIC COMPOUND | COMMENTS, YIELDS, ANALYSIS |
|---|---|---|---|
| 7 | $CH_3CHC \equiv CCHCH_3$<br>\|$\quad\quad\quad\quad$\|<br>OH$\quad\quad\quad\quad$OH<br>3-hexyne-2,5-diol | $CH_3-CH-CH-CH-CH-CH_3$<br>$\quad\quad$\|$\quad\quad$\|$\quad\quad$\|$\quad\quad$\|<br>$\quad\quad$OH$\quad$\|$\quad\quad$\|$\quad\quad$OH<br>(NaO)(H)(O)P$\quad$P(O)(H)(ONa)<br>May also have 3,3 isomer | No unsatn. shown by C-13 NMR, complex product due to many isomers present. P-31 NMR, 87% yield |
| 8 | $CH_3$<br>\|<br>$C_2H_5CC \equiv CH$<br>\|<br>OH<br>3-methyl-1-pentyn-3-ol | $CH_3$<br>\|<br>$C_2H_5CCH_2CH[P(O)(H)(ONa)]_2$<br>\|<br>OH | 76% yield |
| 9 | $CH_3$<br>\|<br>$CH_3CC \equiv CH$<br>\|<br>OH<br>3-methyl-1-butyn-3-ol | $CH_3$<br>\|<br>$CH_3CCH_2CH[P(O)(H)(ONa)]_2$<br>\|<br>OH | 78% yield |
| 10 | $C_2H_5$<br>\|<br>$C_4H_9CHCHC \equiv CH$<br>\|<br>OH<br>4-ethyl-1-octyn-3-ol | $C_2H_5$<br>\|<br>$C_4H_9CHCHCH_2CH[P(O)(H)(ONa)]_2$<br>\|<br>OH<br>+<br>$C_2H_5$<br>\|<br>$C_4H_9CHCH-CHCH2[P(O)(H))ONa)]$<br>\|$\quad\quad$\|<br>OH$\quad$P(O)(H)(ONa) | 39% yield<br><br><br><br><br>60% yield |

EXAMPLE 3

A solution of 6.72 g of propargyl alcohol (Aldrich Chemical Co.) (0.12 mole) and 1.5 g of t-butyl peroctoate dissolved in 35 g of denatured ethanol was added dropwise over a period of 3 hours to a stirred solution containing 25.44 g of sodium hypophosphite monohydrate (0.24 mole), 40 g of denatured ethanol and 20 g of deionized water. The temperature was maintained at 80° C. throughout the addition. After the addition was completed, heating at 77–80° C. was continued for 3 hours longer. During the addition and during the post heat, solids precipitated and began to stick to the reaction flask resulting in bumping during refluxing. The reaction mixture was left to cool and the fine precipitate settled to form a pasty mass on the bottom of the flask. The pasty product was filtered through a sintered glass funnel but soon plugged the sintered glass and filtered very slowly. When a thickened paste was obtained, the filter funnel and pasty precipitate were placed in a vacuum oven and dried at about 50° C. and at 1 mm Hg vacuum for 24 hours forming a hard, white, hygroscopic, foamed solid, 16.6 g. The filtrate was concentrated on a rotary evaporator and then was dried in a vacuum oven at 60° C. and at 1 mm Hg vacuum for 16.6 hours. The dried product was a fluffy, brittle, white solid, 11.5 g. Total weight of the both products was 28.1 g, representing 100.9% yield which indicates that some solvent was left on the solids.

Both portions of the reaction product were analyzed using $^{31}$P NMR and $^{13}$C NMR. Interpretation of the NMR spectra indicated that both 1,1 and 1,2 diadduct of hypophosphite with propargyl alcohol had occurred with the precipitate containing more 1,1 adduct (disodium 3-hydroxypropyl-1,1-diphosphinate) while the filtrate contained more 1,2 adduct (disodium 3-hydroxypropyl-1,2-diphospinate) and unreacted hypophosphite. Overall yield of adducts was calculated to be 91% based on $^{31}$P NMR spectral data.

EXAMPLE 4

A solution of 12.6 g of 3,5-dimethyl-1-hexyn-3-ol (Aldrich Chemical Co.) (0.1 mole) and 1.5 g of t-butyl peroctoate dissolved in 35 g of denatured ethanol was added dropwise over 3.1 hours to a stirred solution containing 21.2 g of sodium hypophosphite monohydrate (0.2 mole), 40 g of denatured ethanol and 20 g of deionized water. The temperature was maintained at 80° C. throughout the addition. After completion of the addition, heating at 79–80° C. was continued for 4.8 hours longer. A fine white precipitate formed in the reaction mixture during the addition and post heating. The reaction mixture was cooled and the precipitate was filtered off using a sintered glass funnel. The precipitate was washed on the funnel several times with fresh ethanol, air dried on the funnel for 2 hours and finally was dried in a vacuum oven at 1 mm Hg and 60° C. for 24 hours. Dry weight of the precipitate was 21.8 g, a white solid. The filtrate was concentrated on a rotary evaporator and then dried in a vacuum oven at 1 mm Hg at 60° C. for 22 hours to leave 9.6 g of a brittle, puffy, white solid. The precipitate was analyzed by $^{13}$C and $^{31}$P NMR and was identified as nearly pure disodium 3,5-dimethylhexyl-3-ol-1,1-diphosphinate, the product resulting from 1,1-diaddition of hypophosphite to the acetylenic bond of 3,5-dimethyl-l-hexyn-3-ol. Phosphorous $^{31}$NMR analysis of the dried filtrate from the reaction showed that about half of it was unreacted hypophosphite and the remaining half was organophosphorous compounds, probably 1,2-diadduct of hypophosphite to the acetylenic compound. Neglecting organophosphorous compounds in the filtrate, the yield of the main product was 72.2%.

EXAMPLES 5-10

The reactions for Examples 5-10 were conducted using the procedures as described for Examples 1-4. Results of these reactions are listed in Table 2. Acetylenic compounds used in these reactions were 2-butyn-1,4-diol, 1-hexyne,2-hexyne-2,5-diol, 3-methyl-1-pentyn-3-ol, 3-methyl-1-butyn-3-ol and 4-ethyl-1-octyn-3-ol.

Reactions with Diphosphinate Compounds

The novel diphosphinic compounds of this invention can be utilized to prepare novel diphosphonic compounds by oxidation of the diphosphinates as shown in the following reaction and as illustrated by Example 11.

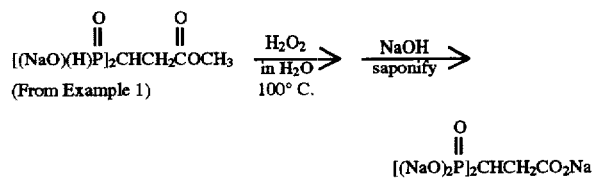

Similarly diphosphinate salt compounds from Example 3, Example 4 and Example 6 were oxidized to form the corresponding diphosphonate salt compounds using hydrogen peroxide (see Example 12, 13, 14). The reaction products were analyzed by $^{31}$P NMR which indicated that some degradation had occurred during oxidation as shown by the presence of some ortho phosphate in the reaction mixture. Other oxidizing agents such as hypochlorite, bromine water, nitric acid, oxygen and the like, may be used with care in order to minimize degradation of the diphosphinate molecule.

The diphosphinate salt compounds of this invention can also be used as chain transfer agents in reactions with unsaturated carboxylic acids and salts of chain length not more than 18 carbon atoms, such as maleic acid, acrylic acid, methacrylic acid, itaconic acid, citraconic acid, aconitic acid, crotonic acid and oleic acid. Polycarboxylic acid-diphosphinate salt adducts and oligomers result from these reactions as illustrated by the reactions with acrylic and maleic acid in FIG. 4 and as described in Examples 15 and 16. A procedure similar to that employed in U.S. Pat. No. 5,085,794 is utilized in the reaction of maleic acid with the diphosphinate compound as illustrated in Example 15. Acrylic acid is reacted with the diphosphinate compound using a procedure similar to that described in U.S. Pat. No. 4,239,648 (to Ciba-Geigy) for reaction of acrylic acid with sodium hypophosphite. Ammonium persulfate initiator is used for the reactions of diphosphinate compounds with both acrylic acid and maleic acid. Other common free radical initiators, such as inorganic peroxides, hydroperoxides and azo-type initiators may be used.

As shown in FIG. 4, mixtures of products result from the reaction of diphosphinate salt compounds with unsaturated acids such as acrylic and maleic acid. When the diphosphinate compound is a mixture of both 1,1 and 1,2 diaddition products of hypophosphite, the reaction with acrylic acid produces a mixture of the two types of polymers shown in FIG. 4. Reacting the mixtures of diphosphinate compounds with 2 moles of maleic acid produces a complex mixture consisting of two types of 2:1 adducts of maleic acid and diphosphinate compounds and two types of oligomeric products as shown in FIG. 4, based on $^{31}$p NMR analysis.

Diphospinate salt compounds may also be used in condensation polymerization reactions with formaldehyde (2 mole) and primary amines (1 mole) per mole of diphosphinate compound as shown in the general reaction that follows:

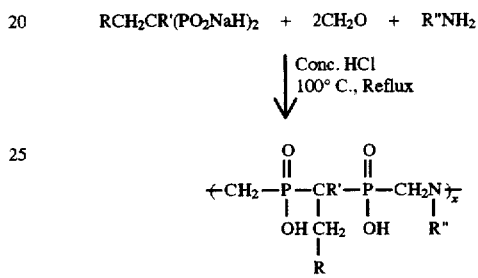

Reaction conditions are those which are used in the Irani phosphonomethylation reaction [Moedritzer and Irani, J. O. C., 31 1603 (1966)]. Polymers that result from this reaction may have a wide variety of substituents on them depending on the substituents from the primary amine used as well as those from the diphosphinate compound. Example 17 illustrates this type of reaction in which glycine (NH$_2$CH$_2$CO$_2$H) is used as the amine. Other common primary amines may be used such as alkyl amines of chain length not more than 18 carbon atoms, amino acids such as glycine, alanine, aspartic acid, glutamic acid, taurine, aminobenzoic acid, aminomethanesulfonic acid, sulfanilic acid and salts of the acids, ethanolamine, aniline, substituted anilines, cyclohexylamine, 6-aminocaproic acid, (aminomethyl) phosphonic acid and salts and (aminoalkyl)phosphonic acids and salts.

EXAMPLE 11

A solution of disodium methyl 3,3-diphosphinicopropionate (Example 1) (5 g., 0.0192 mole) and deionized water (11 g) was heated at 72° C. and hydrogen peroxide (35%) (4.11 g=1.438 g H$_2$O$_2$, 0.0423 mole) (10% molar excess) was added all at once. The solution was slowly heated to reflux over 2.5 hours, and was held at reflux for 9.5 hours longer. At the end of the heating period, the reaction solution was cooled and 50% sodium hydroxide solution (4.615 g, 0.0577 mole) and 25 g deionized water were added. The solution was heated at 85–93° C. for 5 hours to saponify the methyl ester. Analysis of the resulting solution by $^{31}$p and $^{13}$C NMR indicated that the product was pentasodium 3,3-diphosphonopropionate. Concentration of the solution was 18.6%, calculated as disodium 3,3-diphosphonopropionic acid.

EXAMPLE 12

A solution of disodium 3-hydroxypropyl-1,1-diphosphinate (Example 3) (5.0 g, 0.0216 mole) dissolved in deionized water (16 g) was heated to 51° C. and hydrogen peroxide (35%) (4.61 g=1.613 g $H_2O_2$, 0.0474 mole) (10% mole excess) was added all at once. The solution was heated to reflux over 25 minutes and held at reflux for 4 hours. At the end of this time, the solution was cooled and 50% sodium hydroxide (3.35 g, 0.0419 mole) was added (to pH 13) to form the tetrasodium salt of 3-hydroxypropyl-1,1-diphosphonic acid. Concentration of the solution calculated as the free diphosphonic acid was 13.9%. Analysis of the sample by $^{13}C$ and $^{31}p$ NMR indicated that some degradation had occurred during oxidation.

EXAMPLE 13

A solution of disodium 3,5-dimethylhexane-3-ol-1,1-diphosphinate (Example 4) (5.0 g, 0.0166 mole) dissolved in deionized water (17g) was heated to 50° C. and hydrogen peroxide (35%) (3.54 g=1.239 g $H_2O_2$, 0.0364 mole) (10% molar excess) was added all at once. The solution was slowly heated to reflux over 2 hours and was held at reflux for 9.5 hours longer. The solution was left to cool and 50% sodium hydroxide (2.0 g., 0.0250 mole) was added to pH 13 to form the tetrasodium salt of 3,5-dimethylhexane-3-ol-1,1-diphosphonic acid. Analysis by $^{31}P$ NMR indicated that all P-H bonds had been oxidized but some degradation had occurred. Concentration of the sample solution calculated as the free diphosphonic acid was 19.65%.

EXAMPLE 14

A solution of disodium 1,1-hexyl-diphosphinate (Example 6) (5.0 g, 0.0194 mole) dissolved in 25 g of deionized water was heated to 80° C. in 10 minutes and hydrogen peroxide (35%) (4.15 g=1.452 g $H_2O_2$, 0.0427 mole) (10% molar excess) was added. The solution was heated to reflux and held at reflux for 14 hours. The solution was then cooled and 50% sodium hydroxide (2.9 g, 0.0363 mole) was added to pH 13 to form tetrasodium 1, 1-hexyl-diphosphonate. Concentration of the solution calculated as the free diphosphonic acid was 11.7%. Analysis of the sample by $^{31}P$ NMR indicated that most of the P-H bonds were oxidized but some degradation had occurred.

EXAMPLE 15

A solution of disodium 3-hydroxypropyl-1,1-diphosphinate (Example 3) (5.0 g, 0.215 mole) dissolved in deionized water (18 g) was heated to 60° C. with nitrogen purging and to this was added a 33.84% solution of maleic acid (5.0 g., 0.0431 mole) prepared from maleic anhydride (4.22 g, 0.0431 mole) dissolved in deionized water (10.56 g) over 2.5 hours. In a separate addition to the diphosphinate solution was also added ammonium persulfate solution (20%) (5g) over the 2.5 hour period. Heating at 60° C. was continued for 4.5 hours. Additional ammonium persulfate solution (10% solution) (2 g) was then added and heating at 60° C. was continued for 3.5 hours longer. At the end of this time, the reaction solution was cooled and 50% sodium hydroxide (8.73 g, 0.109 mole) was added to pH 13. Concentration of the resulting solution calculated as the disodium salt of the 2:1 adduct of maleic acid with the diphosphinate was 19.72%. Analysis of the sample by $^{31}p$ NMR showed the 70.8M% of the diphosphinic compound had reacted to give a complex mixture of oligomeric product and some 2:1 adduct in addition to 29.2 M % unreacted diphosphinic compound.

EXAMPLE 16

A solution of disodium 3-hydroxypropyl-1,1-diphosphinate (Example 3) (7.0 g., 0.0302 mole) dissolved in deionized water (15 g) was heated to 60° C. With nitrogen purging, a solution of acrylic acid (4.34 g., 0.0603 mole) dissolved in deionized water (13.66 g) was slowly added over 2 hours. In a separate addition but simultaneously, ammonium persulfate solution (9 g) (12.5% solution) was also added over 2 hours. Heating at 60° C. was continued for 3 hours longer before the reaction was stopped and cooled. The reaction solution was analyzed by $^{31}p$ NMR and $^{13}C$ NMR and showed no unreacted acrylic acid. New phosphorus compound peaks were found but not all diphosphinic compound reacted. Molecular weights of the polymer were found to be $M_n$ 1420, $M_w$ 1820.

EXAMPLE 17

Disodium 3-hydroxypropyl-1,1-diphosphinate (5.0 g, 0.2155 mole), paraformaldehyde (95%) (1.361 g, 0.0431 mole), glycine (1.616 g, 0.0215 mole) and deionized water (14.9 g) were added to a stirred reactor and heated to reflux. To this mixture was added concentrated hydrochloric acid (36.5%) (2.155 g, 0.0215 mole) and the mixture was heated at reflux for 8.7 hours. The resulting solution was analyzed by $^{31}p$ NMR and was found to be a complex mixture of phosphorus compounds. Most of the starting diphosphinic compound had reacted based on $^{31}p$ NMR analysis.

Usefulness of the Diphosphinates and Diphosphonates in Commercial Applications The novel diphosphinates and diphosphonates of the invention have many areas of usefulness. Those compounds containing at least one long aliphatic grouping are good detergents. In the area of industrial water treating they can provide scale and corrosion inhibition to such systems as boilers and cooling towers and in oil well process waters. The polycarboxylic acid-diphosphinate adducts/oligomers and polymers are useful as dispersants and scale inhibitors in cooling towers and boilers, as dispersants for slurries of solids and as scale inhibitors in oil well process waters. The diphosphinates and diphosphonates of the invention can also be used as dental anticalculus agents and for treatment of bone metabolism disorders.

To illustrate the ability of certain of the diphosphinates, diphosphonates and diphosphinate containing reaction products to inhibit scale and corrosion, the following examples are presented.

EXAMPLE 18

Evaluation Of The Diphosphinic Compounds as $CaCO_3$ Scale Inhibitors

1. $CaCO_3$ Scale Inhibitor Testing

Diphosphinate salt compounds prepared from acetylenic starting materials and reaction products of diphosphinate salt compounds were evaluated as $CaCO_3$ scale inhibitors using a titration screening test described generally in U.S. Pat. No. 4,457,847 or in U.S. Pat. No. 5,171,451. Results of these tests are shown in Table 3 expressed as saturation ratios at given dosage levels. The saturation ratio indicates how many times above normal the solution has become supersaturated with $CaCO_3$ before precipitation occurred due to the effect of inhibitor in solution. In Table 3, data for various dosage levels of the sample are listed along with data for various reference inhibitors.

TABLE 3

CALCIUM CARBONATE INHIBITION DATA-TITRATION TEST

| Example No. | Test No. | Compound Structure | Saturation Ratios 5 ppm | 10 ppm | 15 ppm | Comments |
|---|---|---|---|---|---|---|
| 6 | 1 | $CH_3(CH_2)_4CH[P(O)(H)(ONa)]_2$ | 60.8 | 85.4 | 100.8 | |
| 4 | 2 | $(CH_3)_2CHCH_2\underset{\underset{OH}{\|}}{\overset{\overset{CH_3}{\|}}{C}}CH_2CH[P(O)(H)(ONa)]_2$ | — | 37.9 | 48.9 | Contains phosphonic compounds. |
| | 3 | $NaO_2C\ CH_2CH[P(O)(H)(ONa)]_2$ | 27.3 | 30.9 | 40.9 | Example 1 hydrolyzed |
| 3 | 4 | $HOCH_2CH_2CH[P(O)(H)(ONa)]_2$ | 16.1 | 22.5 | 20.7 | 1,2 adduct also present |
| 7 | 5 | $[CH_3CH(OH)CHP(O)(H)(ONa)]_2$ | 14.3 | 14.8 | 12.1 | Some 3,3 adduct present |
| 5 | 6 | $HOCH_2\underset{\underset{(NaO)(H)(O)P}{\|}}{C}H\underset{\underset{P(O)(H)(ONa)}{\|}}{C}HCH_2OH$ | 10.6 | 14.8 | 15.6 | Some 2,2 adduct present |
| | | $\underset{\underset{CO_2H}{\|}}{(CHCH_2)_y}\overset{\overset{O}{\|\|}}{P}\underset{\underset{CO_2H}{\|}}{(CH_2CH)_x}\ \ x+y=4$ ONa | 45.4 | — | — | Belclene 500, Ciba Geigy |
| | | $x+y=16$ | 65.2 | — | — | Belsperse 161, Ciba-Geigy |

$CaCO_3$ Scale Inhibitor Testing of Phosphonate Compounds

Oxidation of the diphosphinate salt compounds to diphosphonate salt compounds resulted in materials with improved calcium carbonate scale inhibition. This is shown in Table 4 where the scale inhibition activity of the diphosphinate compound is compared to that of the corresponding diphosphonate compound.

$CaCO_3$ Scale Inhibition of Phosphinate Compound Derivatives

Calcium carbonate scale inhibition activity of the diphosphinate salt compounds is also improved by using them in polymerization reactions with unsaturated carboxylic acids and in condensation reactions with amines and formaldehyde. The data in Table 5 shows that the propargyl alcohol-dihypophosphite adduct (only the 1,1 adduct is shown but the 1,2 adduct is also present in equal molar amount) has poorer scale inhibition than the products made with maleic acid, acrylic acid and by condensation with glycine. In Table 5 only the products made from the 1,1-diphosphinate are shown but products made from 1,2-diphosphinate are present in equal amounts.

TABLE 4

CALCIUM CARBONATE INHIBITION DATA DIPHOSPHINATE VS. DIPHOSPHONATE COMPOUNDS

| Example No. | Structure | Saturationn Ratio 5 ppm Dosage |
|---|---|---|
| 14 | $CH_3(CH_2)_4CH[P(O)(ONa)_2]_2$ | 80.0 |
| 6 | $CH_3(CH_2)_4CH[P(O)(H)(ONa)]_2$ | 60.8 |
| 12 | $HOCH_2CH_2CH[P(O)(ONa)_2]_2$ | 77.9 |
| 3 | $HOCH_2CH_2CH[P(O)(H)(ONa)]_2$ | 16.1 |
| 11 | $NaO_2CCH_2CH[P(O)(ONa)_2]_2$ | 40.9 |
| 1 | $NaO_2CCH_2CH[P(O)(H)(ONa)]_2$ | 27.3 |
| 13 | $(CH_3)_2CHCH_2\underset{\underset{OH}{\|}}{\overset{\overset{CH_3}{\|}}{C}}CH_2CH[P(O)(ONa)_2]_2$ | 56.6 |
| 4 | $(CH_3)_2CHCH_2\underset{\underset{OH}{\|}}{\overset{\overset{CH_3}{\|}}{C}}CH_2CH[P(O)(H)(ONa)]_2$ | 37.9 (10 ppm) |

TABLE 5

CALCIUM CARBONATE INHIBITION DATA
REACTION PRODUCTS OF DIPHOSPHINATE COMPOUNDS

| Example No. | Structure of Compound | Saturation Ratio 5 ppm Dosage |
|---|---|---|
| 3 | $HOCH_2CH_2CH[P(O)(H)(ONa)]_2$ (Starting Material) | 16.1 |
| 15 | $HOCH_2CH_2CH[P(O)(ONa)-CH(CO_2H)-CH_2(CO_2H)]_2$ (Oligomeric products are also present.) | 58.0 |
| 16 | $H(CHCH_2)_y-P(O)(ONa)-CH(CH_2-CH_2-OH)-P(O)(ONa)-(CH_2CH)_x-H$ with $CO_2H$ end groups (MW 1820) | 48.9 |
| 17 | $+CH_2P(O)(OH)-CH(CH_2-CH_2-OH)-PCH_2N+_x$ with $OH$, $CH_2$, $CO_2H$ substituents | 28.6 |

EXAMPLE 19

Evaluation of Diphosphinate Salt and Diphosphonate Salt Compounds as Corrosion Inhibitors Diphosphinate salt and diphosphonate salt compounds prepared from acetylenic starting materials and reaction products of diphospinate compounds were evaluated as mild steel corrosion inhibitors. Results of these tests are shown in Table 6. An electrochemical screening test was used for this evaluation. The experimental section is as follows:

Experiments

In the experiments below, several tests were performed. These tests are summarized as follows:

Saturation Ratio Test

A test solution is prepared by adding calcium, magnesium, inhibitor test polymer and bicarbonate to deionized water. Initial concentrations of the salts should be: 360 ppm $Ca^{+2}$, 200 ppm $Mg^{+2}$, 500 ppm $HCO_3$—(all as $CaCO_3$) and 5, 10, or 15 ppm of inhibitor test polymer as polymer actives/solids. The temperature is maintained at 140° F. (60° C.); the solution is stirred at all times, and the pH is continuously monitored. The solution is titrated with dilute NaOH at a constant rate. With the addition of NaOH, the pH of the test solution slowly increases, then decreases slightly, and increases again. The maximum pH, prior to the slight decrease at precipitation, is the breakpoint pH. A mineral solubility computer program is then used to calculate the calcium carbonate supersaturation ratio based on test conditions at the breakpoint pH. This supersaturation ratio is related to the calcium carbonate inhibition performance. The test procedure is repeated for different inhibitor solutions and dosages. All precipitated calcium carbonate must be removed from the test apparatus with dilute HCl prior to the next test run.

The Saturation Ratio calculation is described in a paper entitled "Computerized Water Modeling in the Design and Operation of Industrial Cooling Systems" presented at the 41st Annual Meeting at the International Water Conference in Pittsburgh, Pa. Oct. 20–22, 1980. This paper is incorporated herein by reference.

The Saturation Ratio test is dependent on the formation of scale above a certain critical pH. Consequently, sodium hydroxide is added to the test solution to increase the pH and supersaturate the test water until the breakpoint pH is achieved. Nucleation and crystal growth occur during the test period. The breakpoint pH is used in a computer program described in the paper above to calculate the saturation ratio values. This value is simply an index for predicting the tendency toward calcium carbonate precipitation. The computer program calculates the saturation ratio based on water composition, operating conditions, temperature, breakpoint pH, cycles of concentration, and acid pH control. The program also compensates for temperature, ionic strength and ion pairing effects. The greater the saturation ratio, the better the polymer is as a scale inhibitor.

Electrochemical Test

Both the Tafel plots and linear polarization resistance tests are conducted in the same water chemistry and conditions. The test solution for the electrochemical corrosion cell is prepared by adding calcium, magnesium, various inhibitors, and bicarbonate to deionized water to obtain 360 ppm $Ca^{+2}$, 200 ppm $Mg^{+2}$, 440 ppm $HCO_3$ (all as $CaCo_3$). Temperature is maintained at 120° F. and the solution is aerated throughout the test period. The pH is uncontrolled. A standard three electrode cell is assembled for the polarization studies. Pre-polished mild steel specimens were used as the rotating working electrode, at a speed of 500 rpm. All potential measurements are made against a saturated calomel reference electrode. Two graphite rods are used as the counter electrode. Polarization resistance measurements are conducted within±20 mV of the corrosion potential at a scan rate of 0.1 mV/sec. Tafel plots are performed by polarizing the mild steel specimen at 20 mV cathodically and anodically from the corrosion potential.

The electrochemical test provides for measurement of Tafel plots and linear polarization resistance data to measure corrosion inhibition activity. This activity is reported as a corrosion rate, and the lower the corrosion rate, the better the test compound is as a corrosion inhibitor.

Corrosion rates of 1 MPY or less are considered as necessary for good corrosion inhibition. All samples were evaluated in a formulation containing 10 ppm of the test compounds, 10 ppm of phosphonobutanetricarboxylic acid (PBTC) and 15 ppm of a proprietary sulfonic containing polymeric dispersant-scale inhibitor. The data from Table 6 shows that Example 7, 12, and 13 are effective as mild steel corrosion inhibitors. The diphosphinate compounds, 3 and 4, corresponding to diphosphonate compounds 12 and 13 are poor corrosion inhibitors. Reaction of Example 3 diphosphinate compound with maleic acid (Example 15) and acrylic acid (Example 16) improved corrosion inhibition of the resulting oligomer or polymer but not enough to make them good corrosion inhibitors.

TABLE 6

ELECTROCHEMICAL SCREENING TESTS DIPHOSPHINIC AND DIPHOSPHONIC COMPOUNDS

| Sample No. | Sample structure | Corrosion Rate (mpy) | Comments |
|---|---|---|---|
| Ex. 7 | CH$_3$CHCH——CHCHCH$_3$<br>   \|        \|<br>  OH      OH<br>H—P=O  H—P=O<br>   \|        \|<br>  ONa    ONa | 0.834 | 3,4 isomer shown, 3,3 isomer also present. |
| Ex. 12 | HOCH$_2$CH$_2$CH(PO$_3$Na)$_2$ | 1.03 | Sample also contains 1,2 diphosphonate compound. |
| Ex. 13 | (CH$_3$)$_2$CHCH$_2$CCH$_2$CH(PO$_3$Na$_2$)$_2$<br>                \|<br>              CH$_3$<br>                \|<br>              OH | 1.22 | |
| Ex. 3 | HOCH$_2$CH$_2$CH(PO$_2$HNa)$_2$ | 4.28 | Sample also contains 1,2 diphosphinate compound. |
| Ex. 4 | (CH$_3$)$_2$CHCH$_2$CCH$_2$CH(PO$_2$HNa)$_2$<br>                \|<br>              CH$_3$<br>                \|<br>              OH | 5.53 | |
| Ex. 15 | HOCH$_2$CH$_2$CH(P——CH——CH$_2$)$_2$<br>          ‖       \|       \|<br>          O    CO$_2$H  CO$_2$H<br>          \|<br>         ONa | 3.01 | Sample contains oligomers and products from 1, 2 diphosphinate isomer. |
| Ex. 16 | H—(CHCH$_2$)y—P——CH—P—(CH$_2$CH)x—H<br>     \|          ‖    \|   ‖        \|<br>   CO$_2$H     O   CH$_2$ O     CO$_2$H<br>              \|    \|   \|<br>            ONa CH$_2$ ONa<br>                  \|<br>                 OH | 3.43 | MW 1820, polymer prepared from 1,2-diphosphinate isomer is also present. |

Test conditions:
120° F., 500 rpm rotating specimen, water chemistry of: 360 ppm Ca/200 ppm Mg/440 ppm HCO$_3^-$ (all as CaCO$_3$), pH uncontrolled, air agitation, mild steel specimen.

We claim:

1. A method for making compounds having the formula:

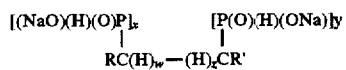

and mixtures thereof where R and R' are radicals from the group consisting of H, alkyl, hydroxyalkyl, alkyl carboxylate, carboxyl, carboxylate, cycloaliphatic and substituted cycloaliphatic, phenyl and substituted phenyl and each do not contain more than 18 carbon atoms, x and y are integers ranging between 0–2 with the sum of x+y being equal to 2, w and z are integers having a value ranging between 0–2 which comprises the steps of reacting a compound of the formula:

with at least two moles of sodium hypophosphite in the presence of polar solvent soluble free radical catalyst and then recovering the produced compounds.

2. The method of claim 1 where R is a hydroxyalkyl group and R' is R or H.

3. The method of claim 1 where R is

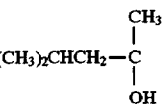

and R' is R or H.

4. The method of claim 1 where R is H or CH$_3$(CH$_2$)m m=0–17) and R' is R or H.

5. The method of claim 1 where R is carboxyl, carboxylate or alkyl carboxylate and R' is R or H.

6. The method of claim 1 where R is

and R' is R or H.

7. An organophosphonate comprising a compound having the formula:

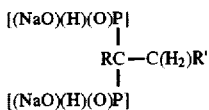

wherein R and R' are radicals selected from the group consisting of H, alkyl, hydroxyalkyl, alkyl carboxylate, carboxyl, carboxylate, cycloaliphatic and substituted cycloaliphatic, phenyl and substituted phenyl and each do not contain more than 18 carbon atoms.

8. The organic phosphinate of claim 7 where R is a hydroxyalkyl group and R' is R or H.

9. The organic phosphinate of claim 7 where R is

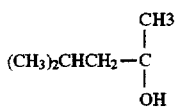

and R' is R or H.

10. The organic phosphinate of claim 7 where R is carboxyl, carboxylate or alkyl carboxylate and R' is R or H.

11. The organic phosphinate of claim 7 where R is

and R' is R or H.

12. A method for making compounds having the formula:

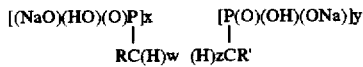

and mixture and salts thereof where R and R' are radicals from the group consisting of H, alkyl, hydroxyalkyl, alkyl carboxylate, carboxyl, cycloaliphatic and substituted cycloaliphatic, phenyl and substituted phenyl and each do not contain more than 18 carbon atoms, x and y are integers ranging between 0-2 with the sum of x+y being equal to 2, w and z are integers having a value ranging between 0-2 which comprises the step of oxidizing the organic phosphinate compounds of claim 7.

13. An organophosphinate comprising a compound having the formula:

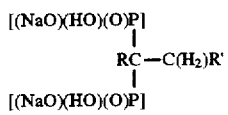

wherein R and R' are radicals selected from the group consisting of H, alkyl, hydroxyalkyl, alkyl carboxylate, carboxyl, carboxylate, cycloaliphatic and substituted cycloaliphatic, phenyl and substituted phenyl and each do not contain more than 18 carbon atoms.

14. The organic phosphonate of claim 13 where R is a hydroxyalkyl group and R' is R or H.

15. The organic phosphonate of claim 13 where R is

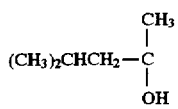

and R' is R or H.

16. The organic phosphonate of claim 13 where R is carboxyl, carboxylate or alkyl carboxylate and R' is R or H.

17. The organic phosphonate of claim 13 where R is

and R' is R or H.

18. The method for making polycarboxylic acid-diphosphinate salt adducts and oligomers by reacting unsaturated carboxylic acids and salts thereof of chain length not more than 18 carbon atoms comprising acrylic acid, maleic acid, methacrylic acid, itaconic acid and oleic acid with the compounds of claim 7 using a free radical initiator.

19. The method of claim 18 where the unsaturated acid is acrylic acid or salts.

20. The method of claim 18 where the unsaturated acid is maleic acid or salts.

21. The method for making condensation polymers using the compounds of claim 7 by reacting them with two moles of formaldehyde and one mole of primary amine per mole of diphosphinate compound under highly acidic conditions.

22. The method of claim 21 where the primary amine is glycine, aspartic acid, glutamic acid or salts of the acids.

23. The method of claim 21 where the primary amine is taurine, aminomethanesulfonic acid, sulfanilic acid or salts of the acids.

24. The method of claim 21 where the primary amine is (aminomethyl)phosphonic acid, (aminoalkyl)phosphonic acid or salts of the acids.

* * * * *